(12) United States Patent
Ishii et al.

(10) Patent No.: US 8,607,472 B2
(45) Date of Patent: Dec. 17, 2013

(54) HAND DRYER

(75) Inventors: Hikoya Ishii, Osaka (JP); Hisaharu Yagi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 345 days.

(21) Appl. No.: 13/144,247

(22) PCT Filed: Nov. 12, 2009

(86) PCT No.: PCT/JP2009/069244
§ 371 (c)(1),
(2), (4) Date: Jul. 12, 2011

(87) PCT Pub. No.: WO2010/089927
PCT Pub. Date: Aug. 12, 2010

(65) Prior Publication Data
US 2011/0277342 A1    Nov. 17, 2011

(30) Foreign Application Priority Data
Feb. 6, 2009    (JP) ................................. 2009-026161

(51) Int. Cl.
*F26B 25/06*    (2006.01)
(52) U.S. Cl.
USPC ............. 34/526; 34/202; 225/10; 285/136.1; 261/117; 15/97.1; 4/654
(58) Field of Classification Search
USPC .......... 34/90, 526, 202, 79, 82; 225/2, 10, 40; 285/94, 136.1, 343; 261/37, 117, 160; 15/97.1, 353, 339; 4/420, 597, 654
See application file for complete search history.

(56) References Cited

U.S. PATENT DOCUMENTS

| | | | |
|---|---|---|---|
| 2,249,624 A * | 7/1941 | Bichowsky | 34/473 |
| 2,438,762 A * | 3/1948 | McLeckie | 34/87 |
| 2,472,272 A * | 6/1949 | Barnes | 34/95 |
| 3,305,938 A * | 2/1967 | Goldstein | 34/546 |
| 3,507,050 A * | 4/1970 | Klaus et al. | 34/265 |
| 4,458,428 A * | 7/1984 | Saeman | 34/506 |
| 4,841,645 A * | 6/1989 | Bettcher et al. | 34/78 |
| 5,673,496 A * | 10/1997 | Wegner et al. | 34/471 |
| 6,038,786 A * | 3/2000 | Aisenberg et al. | 34/267 |

(Continued)

FOREIGN PATENT DOCUMENTS

| | | | |
|---|---|---|---|
| JP | 6-154125 A | | 6/1994 |
| JP | 3028621 U | | 9/1996 |
| JP | 11-56673 A | | 3/1999 |
| JP | 11056673 A | * | 3/1999 |
| JP | 2001-245819 A | | 9/2001 |
| JP | 2002-58731 A | | 2/2002 |
| JP | 2002-306370 A | | 10/2002 |
| JP | 2004-313577 A | | 11/2004 |
| JP | 3630013 B2 | | 3/2005 |
| JP | 2005-342496 A | | 12/2005 |
| JP | 2006-90647 A | | 4/2006 |
| JP | 2010178970 A | * | 8/2010 |
| WO | WO 2010089927 A1 | * | 8/2010 |

*Primary Examiner* — Steve M Gravini
(74) *Attorney, Agent, or Firm* — Birch, Stewart, Kolasch & Birch, LLP

(57) ABSTRACT

A hand dryer is equipped with a hand insertion area (10), having a width that is able to accommodate hands, a high-pressure air generator (2), which generates a high-pressure airflow, discharge nozzles (N1, N2), which are disposed in the upper surface of the hand insertion area (10) and blow the high-pressure airflow, an exhaust duct (4), which is connected between the exhaust side of the high-pressure air generator (2) and the discharge nozzles (N1, N2), an ejection port (23), which opens to the space surrounding the hand dryer, a switching damper (24), which opens a portion of the exhaust duct (4) and is connected to the ejection port (23), and an ion generator (22), which generates ions having sterilization action into the high-pressure airflow passing through the exhaust duct (4) on the upstream side of the switching damper (24).

14 Claims, 6 Drawing Sheets

(56) References Cited

U.S. PATENT DOCUMENTS

| | | | |
|---|---|---|---|
| 6,651,356 B1* | 11/2003 | Buehring | 34/254 |
| 2003/0072675 A1 | 4/2003 | Takeda et al. | |
| 2008/0052952 A1* | 3/2008 | Nelson | 34/554 |
| 2009/0119942 A1* | 5/2009 | Aisenberg et al. | 34/418 |
| 2011/0277342 A1* | 11/2011 | Ishii et al. | 34/526 |
| 2013/0031799 A1* | 2/2013 | Gagnon et al. | 34/526 |
| 2013/0048103 A1* | 2/2013 | Kissel, Jr. | 137/357 |

* cited by examiner (a)

(b)

(a)

(b)

HAND DRYER

TECHNICAL FIELD

The present invention is related to a hand dryer for sanitarily drying wet hands after being washed.

BACKGROUND ART

A hand dryer is a device structured such that, when wet hands are inserted into a hand insertion area, a hand detecting sensor detects the hands, and a high-pressure air generator and a heater start operating to blow a jet of heated air through a discharge nozzle into the hand insertion area, to thereby blow away water drops from the hands. Hand dryers are mostly placed in public rest rooms. Public rest rooms are used by unspecified people, and there may be pathogenic bacteria and viruses floating in the air around hand dryers. Thus, in a situation in which a number of people are using a public rest room, there is a risk of air-borne infection by bacteria or viruses occurring to the users while waiting for a turn to use a hand dryer or while using one.

As to air-cleaning devices, public rest rooms are at best provided with ventilating fans, which are, of course, not equipped with a function of actively working on floating bacteria or viruses to kill or inactivate them.

The applicant of the present application proposed before an air conditioner and an air cleaner which are provided with an ion generator that generates positive and negative ions, including mainly $H^+ (H_2O)_m$ and $O_2^- (H_2O)_n$, capable of killing floating bacteria and inactivating floating viruses (see Patent Literature 2). However, provision of air conditioners or air cleaners as described above in a public rest room would increase the facility cost and the maintenance cost. Furthermore, preparing a space for placing them would be another problem. Thus, practically, it is very difficult to provide an air conditioner or an air cleaner in a public rest room.

CITATION LIST

Patent Literature

Patent Literature 1: Japanese Patent No. 3630013 (see Claim 2, paragraphs [0027], [0028], and FIG. 1)
Patent Literature 2: JP-A-2002-058731 (see claim 1 and paragraph [0006])

SUMMARY OF INVENTION

Technical Problem

The present invention has been made in view of the above problems, and an object of the present invention is to provide a simple-structured hand dryer capable of actively working on bacteria and viruses floating in a space therearound to kill or inactivate the bacteria and the viruses.

Solution to Problem

To achieve the above object, according to one aspect of the present invention, a hand dryer blows out a high-pressure airflow generated by a high-pressure air generator into a hand insertion area which is so sized as to be able to accommodate a hand, to have moisture that is adhered on the hand blown away inside the hand insertion area by kinetic energy of the high-pressure airflow, and the hand dryer includes: an ejection port that opens to a space around the hand dryer; a switching damper that is provided to be openable and closable and that, in an open state thereof, opens part of an airflow path extending from the high-pressure air generator to the hand insertion area to make the airflow path communicate with the ejection port; and an ion generator that generates ions having a sterilization function in the high-pressure airflow flowing at an upstream side of the switching damper in the airflow path.

According to this structure, ions having a sterilization function are generated by the ion generator, and mixed in the high-pressure airflow flowing through the airflow path extending from the high-pressure air generator to the hand insertion area. And, when the switching damper is opened, the airflow path and the ejection port communicate with each other, and the ions are discharged through the ejection port into a space around the hand dryer. With this structure, it possible to kill or inactivate bacteria and viruses floating in the space around the device by the function of the ions.

According to another aspect of the present invention, a hand dryer includes: a hand insertion area which is so sized as to be able to accommodate a hand; a high-pressure air generator that generates a high-pressure airflow; a discharge nozzle that is provided in an upper surface of the hand insertion area and blows out a high-pressure airflow; an exhaust duct that is connected between an exhaust side of the high-pressure air generator and the discharge nozzle; an ejection port that opens to a space around the hand dryer; a switching damper that opens part of the exhaust duct to make the exhaust duct communicate with the ejection port; and an ion generator that generates ions having a sterilization function in the high-pressure airflow flowing at an upstream side of the switching damper in the exhaust duct.

According to this structure, ions having a sterilization function are generated by the ion generator and mixed in the high-pressure airflow flowing through the airflow path extending from the high-pressure air generator to the discharge nozzle provided in the upper surface of the hand insertion area. And, when the switching damper is opened, the exhaust duct and the ejection port communicate with each other, and the ions are discharged through the ejection port into the space around the hand dryer. This makes it possible to kill floating bacteria and inactivate floating viruses in the space around the device.

According to the present invention, preferably, the hand dryer structured as described above further includes a hand detecting sensor that detects a hand inserted into the hand insertion area. Here, when the hand detecting sensor detects a hand, the high-pressure air generator is operated with the switching damper closed, and the ion generator is driven, and when the hand detecting sensor does not detect a hand, the high-pressure air generator is operated with the switching damper opened, and the ion generator is driven.

According to this structure, when the hand dryer is in use, the switching damper is closed, and the ions are contained in the high-pressure airflow blown out into the hand insertion area during a drying process, and thereby, various bacteria are removed from the hand as it is dried. On the other hand, when the hand dryer is out of use, the switching damper is opened, and the ions having the sterilization function is discharged through the ejection port into the space around the hand dryer; thereby, bacteria and viruses floating in the space around the device can be killed or inactivated.

According to the present invention, preferably, the hand dryer structured as described above further includes a hand detecting sensor that detects a hand inserted into the hand insertion area. Here, a power stage of the high-pressure air generator is switchable between two power stages of a high power stage and a low power stage such that, when the hand detecting sensor detects a hand, the high-pressure air generator is operated in the high power stage with the switching damper closed, and the ion generator is driven, and when the hand detecting sensor does not detect a hand, the high-pressure air generator is operated in the low power stage with the switching damper opened, and the ion generator is driven.

According to this structure, since the power stage of the high-pressure air generator is lowered when the hand dryer is out or use, it is possible to reduce power consumption.

According to the present invention, preferably, the hand dryer structured as described above further includes a timer. Here, the timer starts counting time at a time point when the hand detecting sensor stops detecting the hand, and the high-pressure air generator is operated in the high power stage until a predetermined period of time elapses after the time point.

According to this structure, since the power stage of the high-pressure air generator is maintained to be high for the predetermined period of time even when the hand dryer is not used, a large amount of ions are discharged concentratedly during a time zone immediately after a user finishes using the hand dryer, which is a time zone when the residual concentration of floating bacteria and viruses is high, and this helps efficiently kill floating bacteria and inactivate floating viruses in the space around the device.

According to the present invention, preferably, the hand dryer having the above structure further includes an ion sensor. Here, the ion sensor starts detecting ion concentration at a time point when the hand detecting sensor stops detecting the hand, and the high-pressure air generator is operated in the high power stage until a predetermined level of ion concentration is detected.

According to this structure, even when the hand dryer is not used, the power stage of the high-pressure air generator is maintained to be high until the ion concentration lowers to the predetermined level, and thus, a large amount of ions are discharged concentratedly during a time zone immediately after a user finishes using the hand dryer, which is a time zone when the residual concentration of floating bacteria and viruses is high, and this helps efficiently kill floating bacteria and inactivate floating viruses in the space around the device.

And, according to the present invention, as the ions having the sterilization function, ions that mainly include $H^+ (H_2O)_m$ ions as positive ions and $O_2^- (H_2O)_n$ ions as negative ions may be preferably used. These ions undergo chemical reactions on surfaces of the floating bacteria and viruses to produce hydroxyl radicals [.OH] or hydrogen peroxides [$H_2O_2$] as active species, and kill floating bacteria and inactivate floating viruses by pulling out hydrogen atoms from protein forming the surfaces of the floating bacteria and viruses. These ions exhibit deodorizing effect through a similar reaction.

Advantageous Effects of Invention

According to the present invention, ions having a sterilization function are generated by the ion generator and mixed in a high-pressure airflow flowing through the airflow path extending from the high-pressure air generator to the hand insertion area. And, when the switching damper is opened, the airflow path and the ejection port communicate with each other, and the ions are discharged through the ejection port into the space around the hand dryer. Thus, it is possible to provide a simple-structured hand dryer capable of actively working on bacteria and viruses floating in the space therearound to kill or inactivate the bacteria and the viruses.

DESCRIPTION OF EMBODIMENTS

Figure 1:
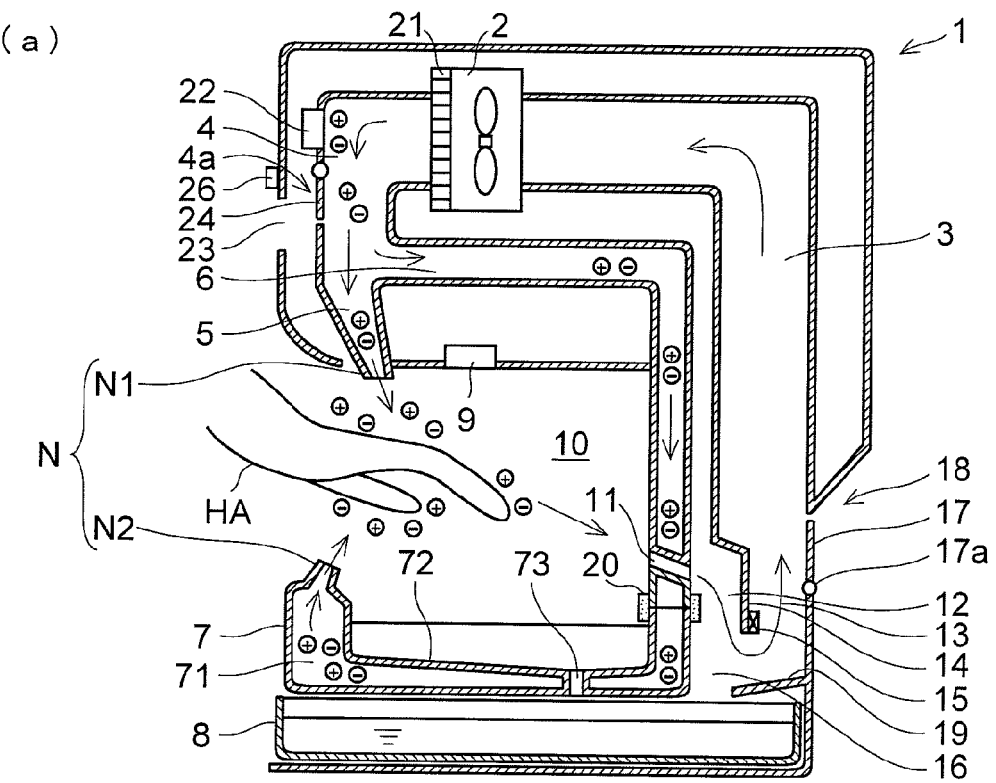
[FIG. 1] Schematic diagrams illustrating the internal structure of a hand dryer according to the present invention, where (a) is a cross-sectional side view showing a state in which air is being sucked in from a hand insertion area during a drying process, and (b) is a cross-sectional side view showing a state in which ambient air is being taken in from outside the device during a drying process.
Figure 1:
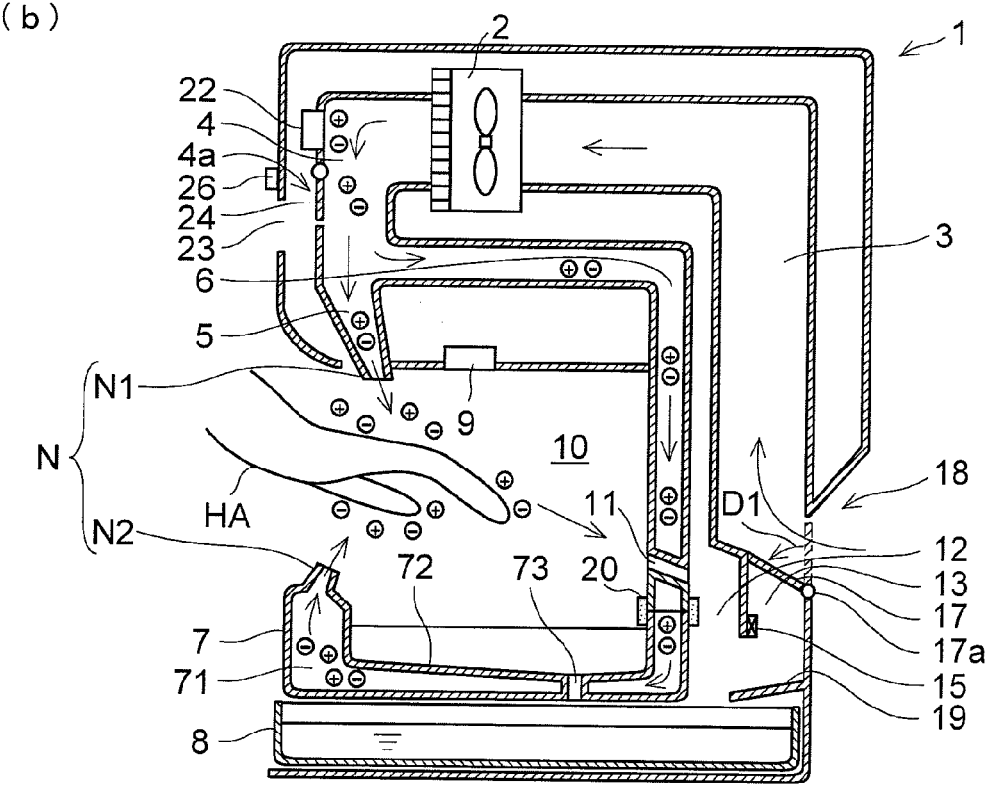
Figure 2:
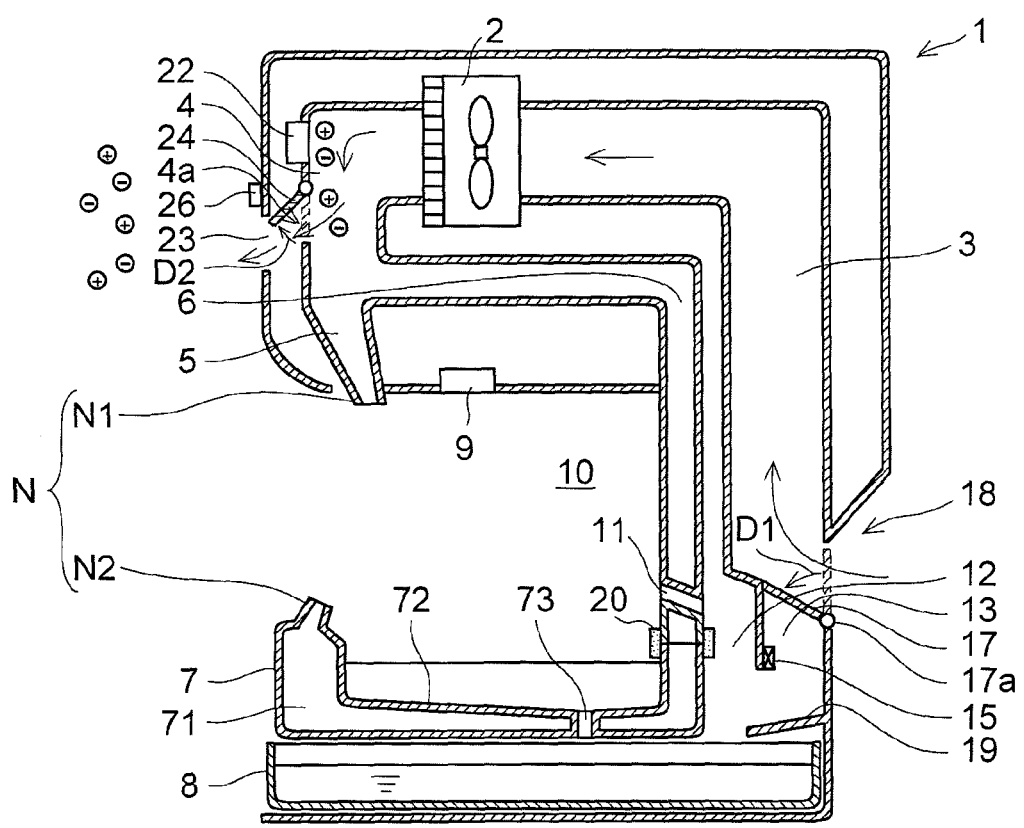
[FIG. 2] A cross-sectional side view schematically illustrating the internal structure of a hand dryer according to the present invention, showing a state in which ions are being discharged into a space therearound after a drying process.
Figure 3:
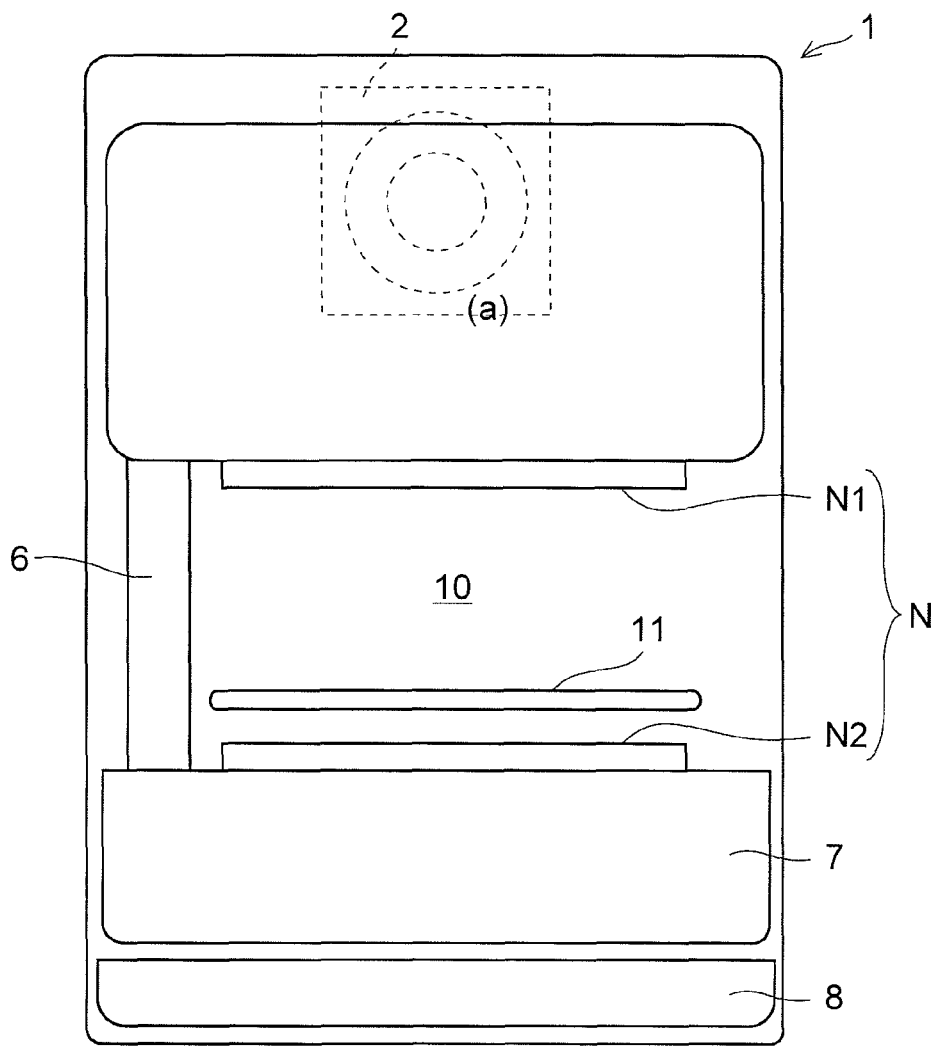
[FIG. 3] Schematic diagrams illustrating a hand dryer according to the present invention, where (a) is a front view, (b) shows another embodiment of a discharge nozzle, and (c) shows another embodiment of a second air-intake port.
Figure 3:
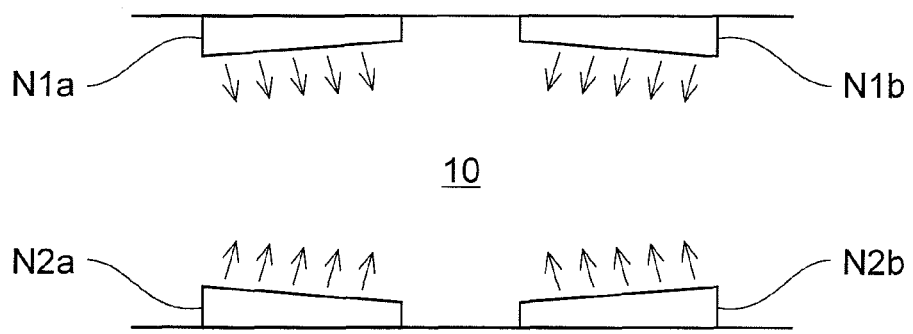
Figure 3:
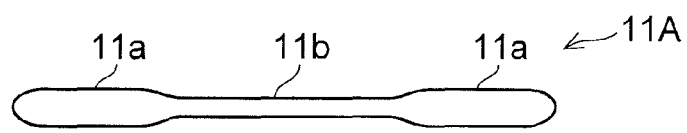
Figure 4:
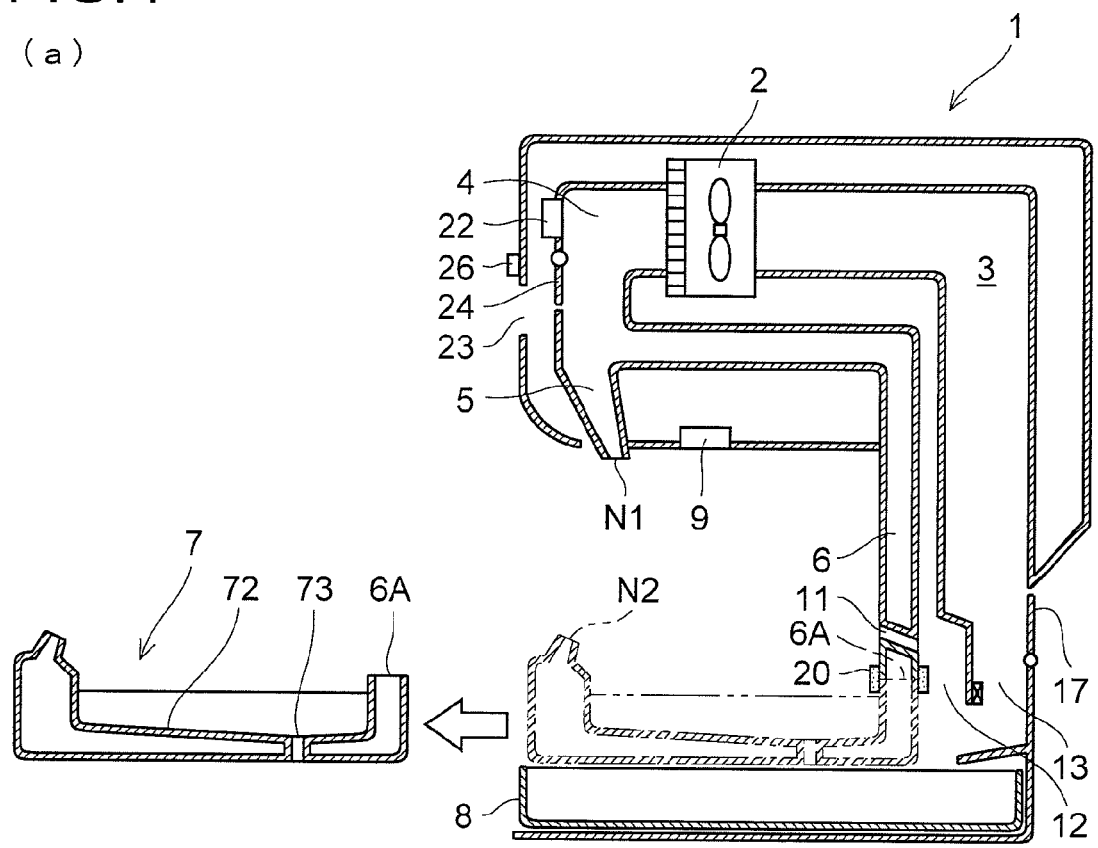
[FIG. 4] Schematic diagrams illustrating a lower tray according to the present invention, where (a) is a cross-sectional side view illustrating how the lower tray is attached and detached, and (b) is a plan view of the lower tray.
Figure 4:
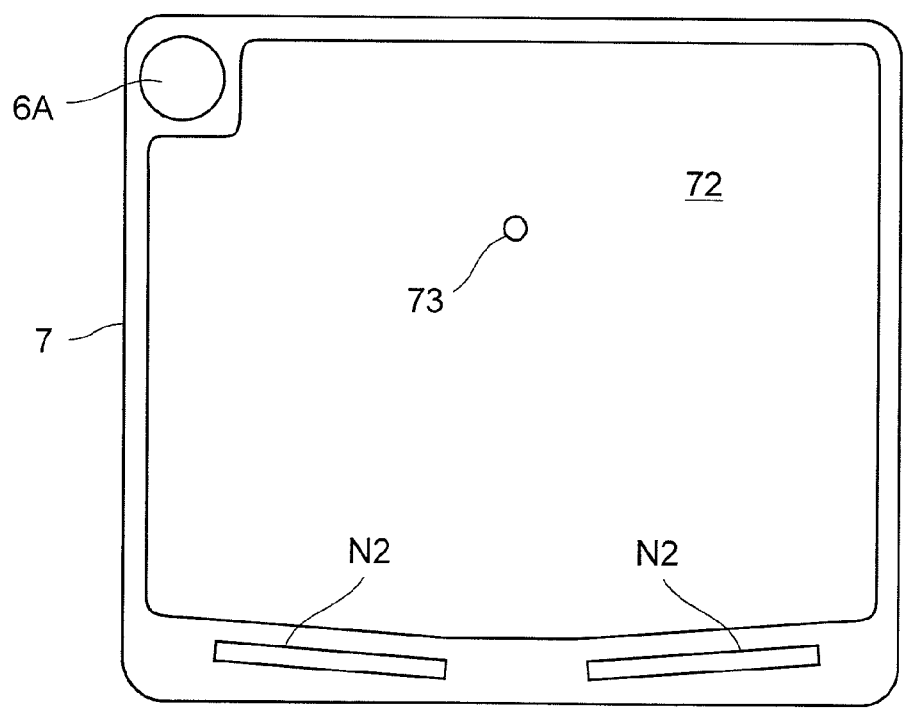
Figure 5:
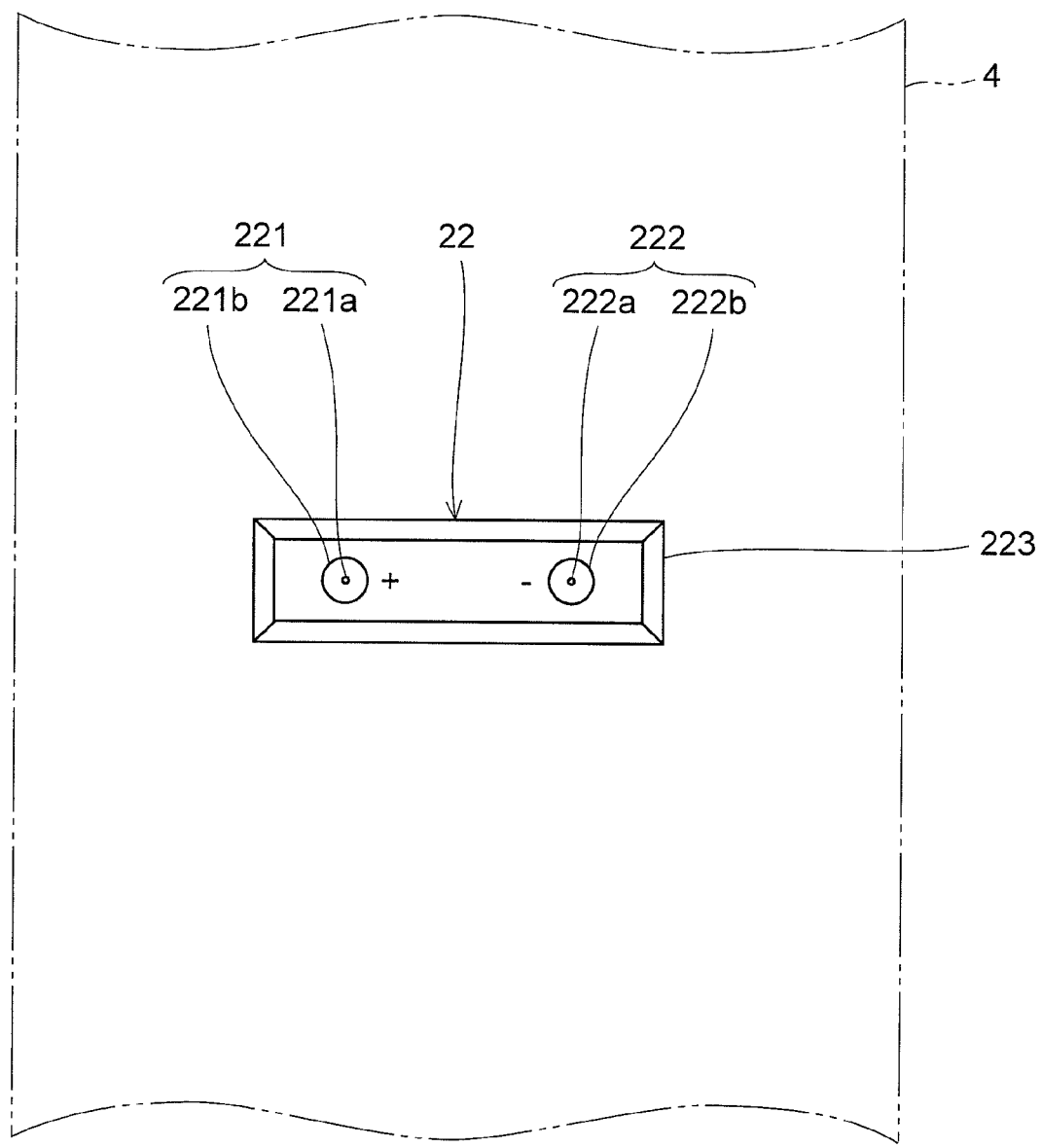
[FIG. 5] A plan view showing the location of an ion generator in an exhaust duct of a hand dryer according to the present invention, as seen from inside the duct.
Figure 6:
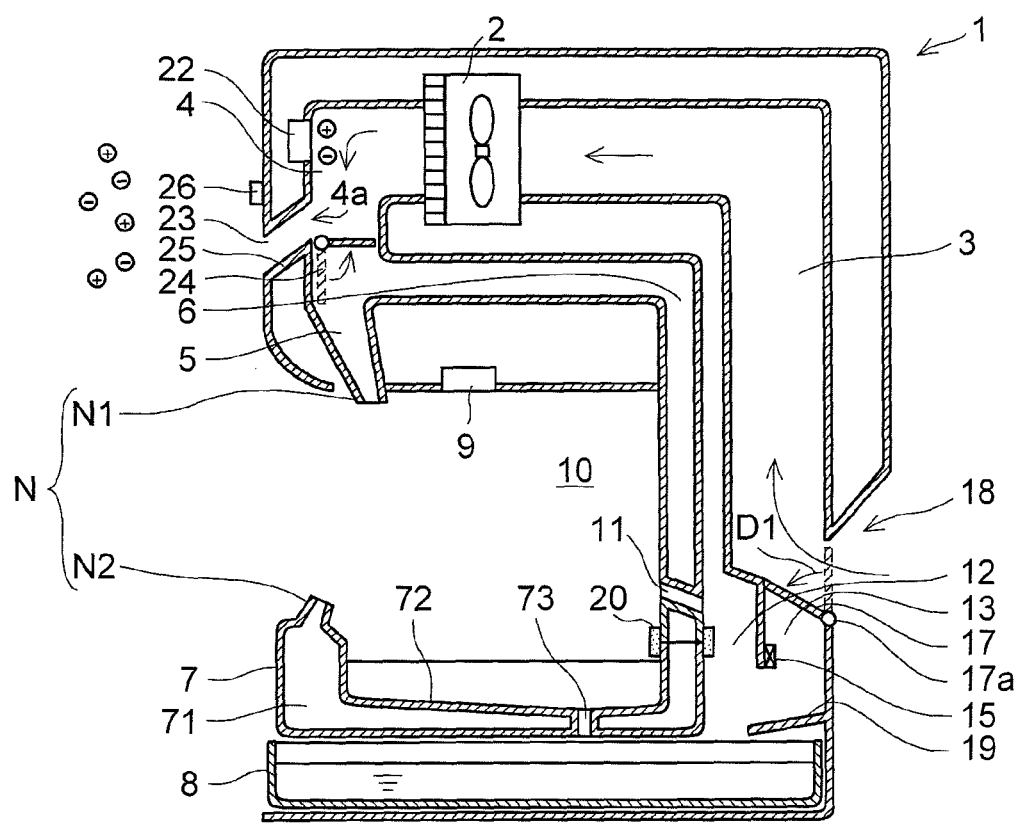
[FIG. 6] A schematic diagram illustrating the internal structure of a hand dryer according to the present invention, showing another embodiment of a switching damper.

Hereinafter, an embodiment of the present invention will be described with reference to the drawings. FIG. 1 includes schematic diagrams illustrating the internal structure of a hand dryer according to the present invention, where (a) is a cross-sectional side view showing a state in which air is being sucked in from a hand insertion area during a drying process, and (b) is a cross-sectional side view showing a state in which ambient air is being taken in from outside the device during a drying process. FIG. 2 is a cross-sectional side view schematically illustrating the internal structure of a hand dryer according to the present invention, showing a state in which ions are being discharged into a space therearound after a drying process. FIG. 3 includes schematic diagrams illustrating a hand dryer according to the present invention, where (a) is a front view, (b) shows another embodiment of a discharge nozzle, and (c) shows another embodiment of a second air-intake port. FIG. 4 includes schematic diagrams illustrating a lower tray according to the present invention, where (a) is a cross-sectional side view illustrating how the lower tray is detached and attached, and (b) is a plan view of the lower tray. FIG. 5 is a plan view showing the location of an ion generator in a exhaust duct of a hand dryer according to the present invention, as seen from inside the duct. FIG. 6 is a schematic diagram illustrating the internal structure of a hand dryer according to the present invention, showing another embodiment of a switching damper. The same components will be identified by common reference symbols, and detailed description of them will be omitted if possible.

First, with reference to FIG. 1, a description will be given of a hand dryer of the present embodiment.

As shown in FIG. 1(a), the hand dryer 1 is provided with a hand insertion area 10 formed substantially in the middle portion of a front surface of a device main body, an air-intake port and an air-intake duct 3, a high-pressure air generator 2, an exhaust duct 4, a discharge nozzle N (N1, N2), and an ejection port 23, and the hand dryer 1 is a device that dries a wet hand HA inserted into the hand insertion area 10 by blowing a jet of high-pressure air to the wet hand HA. The power stage of the high-pressure air generator is switchable between two power stages of a high power stage and a low power stage. Further, as the discharge nozzle N, there are provided an upper discharge nozzle N1 and a lower discharge nozzle N2; when the hand HA is inserted into the hand insertion area 10, a jet of high-pressure air is blown simultaneously to each of front and rear surfaces of the hand HA to dry the hand HA. The ejection port 23 opens in the front surface of the device main body to be located above the hand insertion area 10. Reference numeral 9 denotes a hand detecting sensor provided slightly behind the upper discharge nozzle N1 that is formed in the upper surface of the hand insertion area 10.

Also, it is possible to further improve the drying performance by providing a heater 21 at the discharge port side of the high-pressure air generator 2 to heat the high-pressure air discharged from the high-pressure air generator 2 to send out high-temperature high-pressure air.

Form the exhaust duct 4, an upper exhaust duct 5 and a lower exhaust duct 6 diverge to lead to the upper and lower discharge nozzles N1 and N2, respectively. And, at the upstream side of the diverging point in the exhaust duct 4, there is disposed an ion generator 22 that generates ions having a sterilization function in high-pressure airflow flowing through the exhaust duct 4. Specifically, in a front wall of the exhaust duct 4, through holes are formed corresponding to ion generating portions 221 and 222 (see FIG. 5), and the ion generator 22 is attached by being fitted into the through holes.

As shown in FIG. 5, the ion generator 22 includes: the two ion generating portions 221 and 222, which are located apart from each other in a direction perpendicular to the direction in which air from the high-pressure generator 2 flows; a power supply portion (not shown) that supplies voltage to the ion generating portions 221 and 222; and a holder 223 that holds the ion generating portions 221 and 222 and the power supply portion, the power supply portion supplying voltage to the ion generating portions 221 and 222 to make them perform corona discharge to generate ions.

The ion generating portion 221 has sharp-pointed discharge electrode projections 221a and 222a, and induction electrode rings 221b and 222b surrounding the discharge electrode projections 221a and 222a, respectively, the discharge electrode projections 221a and 222a being arranged in centers of the induction electrode rings 221b and 222b, respectively, such that, as will be described below, the ion generating portion 221, which is located on one side, generates positive ions while the ion generating portion 222, which is located on the other side, generates negative ions. In the ion generating portions 221 and 222, positive ions and negative ions are generated at a level of ten billion ions/cm$^3$, and these ions are immediately sent to the hand insertion area 10 and the like through the sending of the high-pressure air.

That is, positive voltage is applied to the ion generating portion 221, and in a plasma region generated by the discharge, water molecules present in the air are electrically decomposed to produce mainly hydrogen ions H$^+$. Water molecules remaining in the air collect around the produced hydrogen ions to form stable positive cluster ions H$^+$ (H$_2$O)$_m$. To the ion generating portion 222, negative voltage is applied, and in the plasma region generated by the discharge, oxygen molecules present in the air are electrically decomposed to produce mainly oxygen ions O$_2^-$. Water molecules remaining in the air collect around the produced oxygen ions to form stable negative cluster ions O$_2^-$ (H$_2$O)$_m$. Here, "m" and "n" are each any integer. In this specification, the term "positive ion" refers to a positive cluster ion, and the term "negative ion" refers to a negative cluster ion. Incidentally, the production of positive and negative cluster ions has been verified by time-of-flight mass spectrometry.

The positive and negative ions, when simultaneously ejected into the air, collect on surfaces of microorganisms such as bacteria and viruses to surround them. And the positive and negative ions are instantaneously combined to produce and collect, on the surfaces of the microorganisms, hydroxyl radicals [.OH] and hydrogen peroxides [H$_2$O$_2$] as highly oxidative active species, which decompose protein of the surfaces of the microorganisms in a chemical reaction to inhibit the activity of the microorganisms. In addition, it has been ascertained that the hydroxyl radicals [.OH] and hydrogen peroxides [H$_2$O$_2$] produced as described above also function to decompose odor components in the air.

Incidentally, the number and locations of ion generators 22 disposed in the exhaust duct 4 may be appropriately decided or changed according to the required level of ion concentration. For example, two or more ion generators 22 may be arranged side by side apart from each other in the direction in which air from the high-pressure air generator 2 passes, or two ion generators 22 may be arranged apart from each other in the direction in which air from the high-pressure air generator 2 passes, with the orientation of the two ion generators 22 turned by 90°. Furthermore, to increase the amount of ions blown out through the discharge nozzles N1 and N2, there may be provided an ion generator 22 in the diverged exhaust ducts 5 and 6.

The upper discharge nozzle N1 communicates with the high-pressure air generator 2 via the exhaust duct 4 and the upper exhaust duct 5, and the lower discharge nozzle N2 communicates with the high-pressure air generator 2 via the exhaust duct 4 and the lower exhaust duct 6. Also, the lower discharge nozzle N2 is formed to be integral with the lower tray 7 provided in a lower portion of the hand insertion area 10. The lower tray 7 is formed to have a hollow inner portion 71, which is used as an exhaust duct leading to the lower exhaust duct 6, to exhaust high-pressure air from the high-pressure air generator 2 through the lower discharge nozzle N2.

Thus, the high-pressure air sent out via the lower exhaust duct 6 flows through the hollow inner portion 71 of the lower tray 7 to be discharged from the lower discharge nozzle N2. In this way, high-pressure air from the high-pressure air generator 2 flows through the exhaust duct 4 to separately flow into the upper exhaust duct 5 and the lower exhaust duct 6 to be simultaneously discharged from the upper discharge nozzle N1 and the lower discharge nozzle N2, respectively.

Also, a drain tank 8 is provided under the lower tray 7, and a drain hole 73 is formed at a predetermined position in the lower tray 7 to communicate with the drain tank 8. The drain tank 8 is a tank for collecting water drops that fall down into the lower tray 7 or that are away by the high-pressure air. For this purpose, a receiving surface 72 of the lower tray 7 is formed to be inclined downward toward the drain hole 73 such that water drops falling down into the lower tray 7 are all accumulated in the drain tank 8.

With the structure described above, the lower tray 7 provided at a lower portion of the hand insertion area 10 can be used both as a lower exhaust duct and a water-collecting tray.

Further, as the air-intake port, there are provided a first air-intake port 18 through which ambient air is taken in from outside the device, and a second air-intake port (an air-intake port) 11 through which air inside the hand insertion area 10 is taken in; the air-intake duct 3 includes an air-intake flow path 13 that communicates with the first air-intake port 18 and the second air-intake port 11, with a switching damper 17 provided in the air-intake flow path 13, such that the switching damper 17 is switched to make the air-intake flow path 13 communicate with either the first air-intake port 18 or the second air-intake port 11.

For example, by structuring the switching damper 17 to be swingable about a swing support 17a to open/close the first air-intake port 18, it is possible to control the switching damper 17 to swing between two positions, namely, a position for closing the first air-intake port 18 to make the second air-intake port 11 communicate with the air-intake duct 3 as shown in FIG. 1(a), and a position for opening the first air-intake port 18 to communicate with the air-intake duct 3 and close the second air-intake port 11 as shown in FIG. 1(b).

The ejection port 23 is made to communicate with the exhaust duct 4 by a switching damper 24 that opens part of the exhaust duct 4. For example, by structuring the switching damper 24 to be swingable about a swing support 24a to open/close a through hole 4a formed as an opening in the front wall of the exhaust duct 4, it is possible to control the switching damper 24 to swing between two position, namely, a position for closing the through hole 4a such that the ejection port 23 does not communicate with the exhaust duct 4 as shown in FIGS. 1(a) and (b), and a position for opening the through hole 4a to communicate with the exhaust duct 4 as shown in FIG. 2. Incidentally, as shown in FIG. 6, a duct 25 may be provided to connect the ejection port 23 to the through hole 4a, such that the exhaust duct 4 is blocked at the exhaust ducts 5 and 6 side by a switching damper 24 swingably provided in the exhaust duct 4 at a downstream side of the through hole 4a, to make the exhaust duct 4 and the ejection port 23 communicate with each other via the duct 25.

As shown in FIG. 1(a), when the high-pressure air generator 2 is driven in a state in which the first air-intake port 18 is closed, the second air-intake port 11 communicates with the air-intake duct 3, and the through hole 4a is closed such that the ejection port 23 does not communicate with the exhaust duct 4, air is taken in through the second air-intake port 11. The air that is taken in is sent to the air-intake duct 3 from an air-intake chamber 12 via a drain separator 14 and the air-intake flow path 13.

A drain collecting port 16 is provided under the drain separator 14, and when air taken in a gush through the second air-intake port 11 strikes the drain separator 14, water is separated from the air, and the separated water falls down into the drain tank 8. In addition, an inclined plate 19 is provided on a side portion of the device for the purpose of guiding water drops dripping from the drain separator 14 to the drain tank 8.

Reference numeral 15 denotes a humidity sensor, which is capable of detecting the humidity of air that is sent to the air-intake duct 3 after being taken in from the hand insertion area 10 through the second air-intake port 11. The humidity sensor 15 is provided in the vicinity of the drain separator 14, and with information obtained from the humidity sensor 15, it is possible to judge whether or not the air taken in through the second air-intake port 11 contains a large amount of moisture. As a result, when the humidity detected by the humidity sensor 15 is found to be a predetermined level or lower, it is judged that most of water drops on the hand HA have been blown away, and control is carried out to switch the switching damper 17 such that ambient air is taken in from outside the device through the first air-intake port 18 to further accelerate the drying process.

As shown in FIG. 1(b), in a state in which the switching damper 17 is swung about the swing support 17a in the direction of arrow D1 in the figure to close the second air-intake port 11 and open the first air-intake port 18 to communicate with the air-intake duct 3, it is ambient air taken in from outside the device through the first air-intake port 18 that is sent to the high-pressure air generator 2. Thus, air that is sent to the high-pressure air generator 2 is comparatively dry air having a low humidity, which is preferable as high-pressure air for drying hands.

When a wet hand is inserted into the hand insertion portion 10 and the hand detecting sensor 9 detects the hand HA, the high-pressure air generator 2 is activated in the high power stage via an unillustrated control device. At this time, the ion generator 22 is also driven simultaneously. When high-pressure air is blown to the wet hand, water drops are scattered from the surface of the hand HA to the space around the hand HA. In particular, in a case in which the hand insertion area 10 has an opening formed in a side surface thereof, high-pressure air containing water drops or moisture may blow out in the direction of a side surface of the device, to splash on a person or an object present beside the device.

However, as in the present embodiment, with a structure in which the second air-intake port 11 is provided to take in air from the hand insertion area 10, when the high-pressure air generator 2 is driven, a strong sucking force is generated at the second air-intake port 11 to strongly suck in air from the hand insertion area 10. Thus, when high-pressure air is discharged simultaneously from both the upper discharge nozzle N1 and the lower discharge nozzle N2 to dry the hand HA, the discharged high-pressure air and scattering water drops are both sucked in through the second air-intake port 11 to prevent them from being scattered around the surrounding area.

Also, positive and negative ions having a sterilization function and generated by the ion generator 22 are contained in a high-pressure airflow discharged into the hand insertion area 10 through the discharge nozzles N1 and N2 during the drying process, and thereby, various bacteria are eliminated from the hand along with drying of the hand. This makes it possible to realize smooth and quick drying and sterilization of the hand with a simple structure. Moreover, since the discharge nozzle N2 is also provided in the lower surface of the hand insertion area 10, ions having the sterilization function are blown into the hand insertion area 10 upward from the discharge nozzle provided in the lower surface of the hand insertion area 10, and thus mold and various bacteria on the invisible upper surface of the hand insertion area 10, which is out of sight, can also be eliminated. Also, ions having the sterilization function are blown into the hand insertion area 10 not only from the top but also from the bottom of the hand insertion area 10, it is possible to quickly eliminate various bacteria attached to the palm and back of hands without rubbing the hands.

As the drying process is continued for a predetermined period of time while sucking in air through the second air-intake port 11, the hand HA gradually becomes dry. Thus, when the predetermined period of time has elapsed after the start of the drying, the switching damper 17 may be swung to open the first air-intake port 18 to accelerate the drying by using ambient air from outside the device as air for drying. That is, two stages of steps may be set in advance as steps of the hand drying process, that is, a water-drop-blowing-away step that continues for a predetermined period of time after the drying operation is started, and a drying step performed after the water-drop-blowing-away step. Also, instead of driving the switching damper 17 after the predetermined period of time, it is possible to drive the switching damper 17 when the hand HA is judged to have started to get dried, that is, when humidity of a predetermined level or lower is detected by using the above mentioned humidity sensor 15, and it is also possible to automatically control the water-drop-blowing-away step and the drying step as a series of steps.

Also, hand dryers are mostly placed in public rest rooms. Public rest rooms are used by unspecified people, and there may be pathogenic bacteria and viruses floating in the air around hand dryers. Thus, in a situation in which a number of people are using a public rest room, there is a risk of air-borne infection by bacteria or viruses occurring to the users while waiting for a turn to use a hand dryer or while using one.

To cope with these problems, as shown in FIG. 2, when the hand is pulled out from the hand insertion area 10 after it is dried, the hand detecting sensor 9 stops detecting the hand HA, and at this time, the power stage of the high-pressure air generator 2 is switched to the low power stage via the control device, with the ion generator 22 continuing to be driven. Furthermore, the switching damper 24 is swung to make the ejection port 23 communicate with the exhaust duct 4. According to this structure, positive and negative ions having a sterilization function are generated by the ion generator 22, and the ions are mixed in the high-pressure airflow flowing through the exhaust duct 4 extending from the high-pressure air generator 22 to the hand insertion area 10. And, the ions are discharged from the ejection port 23 into the space around the hand dryer. This makes it possible to have bacteria and viruses floating in the space around the hand dryer killed or inactivated by the function of the ions. At this time, since the power stage of the high-pressure air generator 2 is lowered, power consumption is reduced. After a predetermined period of time, the high-pressure air generator 2 and the ion generator 22 are stopped, and the operation of the hand dryer is finished.

At this time, a timer may be used to start counting time at a time point when the hand detecting sensor 9 stops detecting the hand, and the high-pressure air generator 2 may be operated in the high power stage until a predetermined period of time elapses after the time point. According to this structure, since the power stage of the high-pressure air generator is maintained to be high for the predetermined period of time even when the hand dryer is not used, a large amount of ions are discharged concentratedly during a time zone immediately after a user finishes using the hand dryer, which is a time zone when the residual concentration of floating bacteria and viruses is high, and this helps efficiently kill floating bacteria and inactivate floating viruses in the space around the device. Incidentally, two ion generators 22 may be provided to be operated such that both of them are driven until a predetermined period of time elapses after the timer starts counting time, and just either of the ion generators 22 is driven after the predetermined period of time elapses, so as to generate increased amount of ions during a time zone immediately after the use of the hand dryer is finished, which is a time zone when the residual concentration of floating bacteria and viruses is high.

Alternatively, an ion sensor 26 may be provided on the front surface of the device main body, the ion sensor 26 starting to detect the concentration of positive and negative ions at a time point when the hand detecting sensor 9 stops detecting the hand, and the high-pressure air generator may be operated in the high power stage until a predetermined level of ion concentration is detected. According to this structure, even when the hand dryer is not used, the power stage of the high-pressure air generator is maintained to be high until the ion concentration lowers to the predetermined level, and thus, a large amount of ions are discharged concentratedly during a time zone immediately after a user finishes using the hand dryer, which is a time zone when the residual concentration of floating bacteria and viruses is high, and this helps efficiently kill floating bacteria and inactivate floating viruses in the space around the device.

Incidentally, two ion generators 22 may be provided to be operated such that both of them are driven until a predetermined period of time elapses after the timer starts counting time, and just either of the ion generators 22 is driven after the predetermined period of time elapses, so as to generate increased amount of ions during a time zone immediately after the use of the hand dryer is finished, which is a time zone when the residual concentration of floating bacteria and viruses is high.

With a structure in which, when the hand detecting sensor 9 detects the hand HA again, the switching dampers 17 and 24 are swung to make the second air-intake port 11 and the air-intake duct 3 communicate with each other, and the through hole 4a of the exhaust duct 4 is closed, it is possible to stop the high-pressure air generator 2 when a predetermined period of time has elapsed since the hand is pulled out from the hand insertion area 10, regardless of the positions of the switching dampers 17 and 24. Any structure is preferable as long as the following is achieved; that is, in drying a wet hand, the process is first performed with air taken in from inside the hand insertion portion 10; after a predetermined period of time, or after water drops have been blown away from the hand, the drying of the hand is completed with ambient air taken in from outside the device; and, in killing floating bacteria and inactivating floating viruses in the space around the device, ambient air is taken in from outside the device, and positive and negative ions are ejected through the ejection port into the space around the device.

In drying wet hands, both hands are inserted horizontally side by side into the hand insertion area 10 to be dried, and thus, in order to efficiently take in high-pressure air that is discharged from the upper and lower discharge nozzles N1 and N2 to flow to strike the hands, it is preferable that the second air-intake port 11 be provided at a position along a direction pointed by the fingertips of the hand HA when it is inserted. Further, it is preferable that the second air-intake port 11 be formed as a linear air-intake port in a wall surface facing the finger tips of the both hands. If the second air-intake port 11 is formed as an elongate linear air-intake port, the linear air-intake port communicating with the air-intake duct 3 leading to the high-pressure air generator 2 exhibits a suction power as strong as that of the suction port of a vacuum cleaner. This makes it possible to efficiently suck in high-pressure air discharged into the hand insertion area 10 and water drops splashing from hands.

For example, the second air-intake port 11 is formed as an elongate linear air-intake port as shown in FIG. 3(a). However, modified examples other than as shown in FIG. 3(a) are also possible to be adopted; for example, as shown in FIG. 3(c), it is possible to form the second air-intake port 11 as an elongate second air-intake port 11A which includes end-portion suction portions 11a and a central suction portion 11b narrower in width than the end-portion suction portions 11a such that sucked-in air flows faster at the central portion than at the end portions. The second air-intake port 11 may be formed in whichever shape as long as it has a shape and a size suitable to suck in high-pressure air discharged from the discharge nozzles and water drops splashing from hands in drying hands placed horizontally side by side.

As the discharge nozzles N provided at upper and lower portions of the hand insertion area 10, as shown in the front view of FIG. 3(a), the upper and lower discharge nozzles N1 and N2 are formed at the upper and lower portions, respectively, of the hand insertion area 10. These discharge nozzles N are preferably formed to be able to blow high-pressure air across the width of the both hands inserted horizontally side by side. To achieve this, each of the discharge nozzles is formed as a single elongate injection port or as an elongate discharge nozzle composed of a group of a number of small-diameter injection holes.

Also, as shown in FIG. 3(b), it is possible to provide a pair of right and left upper discharge nozzles N1a and N1b discharging air toward a rear-center side of the hand insertion area 10, and a pair of right and left lower discharge nozzles N2a and N2b also discharging air toward the rear-center side of the hand insertion area 10. With this structure, since high-pressure air is discharged toward the center of the rear portion of the hand insertion area 10, it is possible to guide high-pressure air discharged from each of the discharge nozzles and water drops splashing from the hands further effectively to the second air-intake port formed at the rear side of the hand insertion area 10, which is preferable.

Next, a description will be given of the lower tray 7 which is structured to be detachable/attachable, with reference to FIG. 4.

The drain tank 8 is conventionally attachable/detachable to/from the device main body. In the present embodiment, in addition to the drain tank 8, the lower tray 7 is also structured attachable/detachable to/from the device main body.

For example, as shown in FIG. 4(a), if the lower tray 7 is structured to be attachable/detachable by drawing out toward the front of the device main body, when the lower tray 7 is stained, the lower tray 7 can be drawn out to be detached from the device main body to be cleaned. To achieve this, an exhaust duct leading to, and attachable/detachable to/from, the lower exhaust duct 6 is provided on the lower tray 7 side to form a lower exhaust duct composed of separable top and bottom parts, which are airtightly connected to each other at a connection portion at which the lower exhaust duct is separated into the top and bottom parts.

For example, in attaching the lower tray 7 to the device main body, the lower exhaust duct 6 separated from the lower-tray-side exhaust duct is airtightly joined to the lower-tray-side exhaust duct with a seal member such as a sealing gasket therebetween. Also, instead of using the sealing member, a rubber band may be used to cover the joint portion to achieve the sealed connection, such that, as shown in the figure, a pipe-shaped lower-tray exhaust duct 6A is provided in the lower tray 7 to be connected to the pipe-shaped lower exhaust duct 6, the lower-tray exhaust duct 6A and the lower exhaust duct 6 fastened together with the rubber band 20. With this structure, just by sliding the rubber band 20 upward or downward, the connection between the lower exhaust duct 6 and the lower-tray exhaust duct 6A can be released, and the lower tray 7 can be drawn out from the device main body.

In attaching the lower tray 7 to the device main body, for example, the lower tray 7 is pushed in to be set in a predetermined position such that an engagement projection formed on the tray side and an engagement recess formed on the device main body side engage each other. Also, in this pushing-in operation, by pressing the lower-tray exhaust duct 6A against the sealing member attached on the lower exhaust duct 6, the airtight connection can be achieved. Further, in the case of using a rubber band, the lower tray is pushed in to the position where the lower-tray exhaust duct 6A and the lower exhaust duct 6 connect each other and then the connection portion is covered by the rubber band 20 to thereby achieve the airtight connection. In this way, by forming the lower-tray exhaust duct 6A and the lower exhaust duct 6 to be connectable/disconnectable to/from each other to thereby make the lower tray 7 attachable/detachable to/from the device main body, the lower tray 7, when it is stained, can be removed from the device main body to be cleaned, which facilitates the maintenance of the hand dryer.

The lower tray 7, as shown in FIG. 4(b), can be formed as a molding that integrally includes the lower discharge nozzle N2, the lower-tray exhaust duct 6A, the receiving surface 72, and the drain hole 73. Also, from the view point of sanitation, the lower tray 7 is preferably formed as an antibacterial resin blow molding.

If the lower tray 7 is formed as an antibacterial resin blow molding, even if moisture attaches to the lower tray 7, it does not invite increase of bacteria, and thus water and circulating air do not become contaminated with bacteria; this contributes to clean drying of hands, in which wet hands are dried in a sanitary manner without being contaminated with bacteria.

Further, water repellent finishing can be applied to the lower tray 7 formed as a resin molding. With this structure, the surface of the lower tray 7 is stain-resistant and can be maintained in a sanitary state, which contributes to maintaining a state that makes it possible to perform sanitary drying.

Furthermore, components such as the exhaust duct 4, the upper exhaust duct 5, and the lower exhaust duct 6 can also be formed as resin moldings. Thus, by forming these components also as antibacterial resin blow moldings and further applying water repellent finishing to surfaces thereof, it is possible to obtain a hand dryer that is capable of inhibiting increase of germs and that is stain-resistant and thus easy to be maintained in a sanitary state.

With the hand dryer 1 structured as described above, fast drying is realized by the two, upper and lower discharge nozzles N1 and N2; furthermore, since high-pressure air is produced by taking in air from inside the hand insertion area 10, high-pressure air discharged into the hand insertion area 10 and water drops splashing from hands are inhibited from leaking outside the device; thus, a hand dryer is achieved that is, in spite of its compact size, capable of preventing leakage of high-pressure air and dashing-out of water drops, and also capable of reducing time necessary to complete drying.

Also, as air-intake ports, the first air-intake port for taking in ambient air from outside the device and the second air-intake port for taking in air from inside the hand insertion area are provided, and either one of the air-intake ports is closed and the other of the air-intake ports is opened via the switching dampers. Thus, it is possible to dry hands in such a manner that, when the hands are wet, they are dried by circulating air taken in through the second air-intake port from inside the hand insertion area, during which water is inhibited from blowing to the outside, and when the hands become comparatively dry, ambient air taken in from outside the device starts to be used and blown to the hands to accelerate the drying of the hands.

Moreover, since the lower tray is formed attachable/detachable to/from the device main body, the lower tray 7, when it is stained, can be removed from the device main body to be cleaned, which helps keep the hand dryer in a sanitary state and thus facilitates the maintenance of the hand dryer.

It is to be understood that the present invention may be carried out in any other manner than specifically described above as embodiments, and many modifications and variations are possible within the scope of the present invention.

As has been described hereinabove, according to the present invention, ions having a sterilization function is generated by the ion generator, and mixed in high-pressure airflow flowing through the airflow path extending from the high-pressure air generator to the hand insertion area. And, when the switching dampers are opened, the airflow path and the ejection port communicate with each other, and the ions are discharged through the ejection port into the space around the hand dryer. Thus, it is possible to provide a simple-structured hand dryer capable of actively working on bacteria and viruses floating in the space therearound to kill or inactivate the bacteria and the viruses.

INDUSTRIAL APPLICABILITY

With the hand dryer according to the present invention, in drying wet hands, high-pressure air containing moisture and water drops are inhibited from dashing out of the hand dryer, which helps maintain clean state and contributes to easy maintenance. Thus, the hand dryer of the present invention can be preferably used in public places.

LIST OF REFERENCE SYMBOLS 1 hand dryer
2 high-pressure air generator
3 air-intake duct
4 exhaust duct
4a through hole
5 upper exhaust duct
6 lower exhaust duct
6A lower tray exhaust duct
7 lower tray
8 drain tank
9 hand detecting sensor
10 hand insertion area
11 second air-intake port
13 air-intake flow path
14 drain separator
15 humidity sensor
16 drain collecting port
17 switching damper
18 first air-intake port
22 ion generator
23 ejection port
24 switching damper
26 ion sensor
73 drain hole
N1 upper discharge nozzle
N2 lower discharge nozzle

The invention claimed is:

1. A hand dryer that blows out a high-pressure airflow generated by a high-pressure air generator into a hand insertion area which is so sized as to be able to accommodate a hand, to have moisture that is adhered on the hand blown away inside the hand insertion area by kinetic energy of the high-pressure airflow,
the hand dryer comprising:
an ejection port that opens to a space around the hand dryer;
a switching damper that is provided to be openable and closable and that, in an open state thereof, opens part of an airflow path extending from the high-pressure air generator to the hand insertion area to make the airflow path communicate with the ejection port; and
an ion generator that generates ions having a sterilization function in the high-pressure airflow flowing at an upstream side of the switching damper in the airflow path.

2. A hand dryer, comprising:
a hand insertion area which is so sized as to be able to accommodate a hand;
a high-pressure air generator that generates a high-pressure airflow;
a discharge nozzle that is provided in an upper surface of the hand insertion area and blows out a high-pressure airflow;
an exhaust duct that is connected between an exhaust side of the high-pressure air generator and the discharge nozzle;
an ejection port that opens to a space around the hand dryer;
a switching damper that opens part of the exhaust duct to make the exhaust duct communicate with the ejection port; and
an ion generator that generates ions having a sterilization function in the high-pressure airflow flowing at an upstream side of the switching damper in the exhaust duct.

3. The hand dryer of claim 1, further comprising:
a hand detecting sensor that detects a hand inserted into the hand insertion area,
wherein,
when the hand detecting sensor detects a hand, the high-pressure air generator is operated with the switching damper closed, and the ion generator is driven; and
when the hand detecting sensor does not detect a hand, the high-pressure air generator is operated with the switching damper opened, and the ion generator is driven.

4. The hand dryer of claim 1, further comprising:
a hand detecting sensor that detects a hand inserted into the hand insertion area,
wherein
a power stage of the high-pressure air generator is switchable between two power stages of a high power stage and a low power stage;
when the hand detecting sensor detects a hand, the high-pressure air generator is operated in the high power stage with the switching damper closed, and the ion generator is driven; and
when the hand detecting sensor does not detect a hand, the high-pressure air generator is operated in the low power stage with the switching damper opened, and the ion generator is driven.

5. The hand dryer of claim 4, further comprising:
a timer,
wherein
the timer starts counting time at a time point when the hand detecting sensor stops detecting the hand, and the high-pressure air generator is operated in the high power stage until a predetermined period of time elapses after the time point.

6. The hand dryer of claim 4, further comprising:
an ion sensor,
wherein
the ion sensor starts detecting ion concentration at a time point when the hand detecting sensor stops detecting the hand, and the high-pressure air generator is operated in the high power stage until a predetermined level of ion concentration is detected.

7. A hand dryer of claim 1,
wherein
the ions having the sterilization function mainly include $H^+(H_2O)_m$ ions as positive ions and $O_2^-(H_2O)_n$ ions as negative ions.

8. The hand dryer of claim 2, further comprising:
a hand detecting sensor that detects a hand inserted into the hand insertion area,
wherein,
when the hand detecting sensor detects a hand, the high-pressure air generator is operated with the switching damper closed, and the ion generator is driven; and
when the hand detecting sensor does not detect a hand, the high-pressure air generator is operated with the switching damper opened, and the ion generator is driven.

9. The hand dryer of claim 2, further comprising:
a hand detecting sensor that detects a hand inserted into the hand insertion area, wherein
a power stage of the high-pressure air generator is switchable between two power stages of a high power stage and a low power stage;

when the hand detecting sensor detects a hand, the high-pressure air generator is operated in the high power stage with the switching damper closed, and the ion generator is driven; and when the hand detecting sensor does not detect a hand, the high-pressure air generator is operated in the low power stage with the switching damper opened, and the ion generator is driven.

10. A hand dryer of claim 2,
wherein
the ions having the sterilization function mainly include $H^+(H_2O)_m$ ions as positive ions and $O_2^-(H_2O)_n$ ions as negative ions.

11. A hand dryer of claim 3,
wherein
the ions having the sterilization function mainly include $H^+(H_2O)_m$ ions as positive ions and $O_2^-(H_2O)_n$ ions as negative ions.

12. A hand dryer of claim 4,
wherein
the ions having the sterilization function mainly include $H^+(H_2O)_m$ ions as positive ions and $O_2^-(H_2O)_n$ ions as negative ions.

13. A hand dryer of claim 5,
wherein
the ions having the sterilization function mainly include $H^+(H_2O)_m$ ions as positive ions and $O_2^-(H_2O)_n$ ions as negative ions.

14. A hand dryer of claim 6,
wherein
the ions having the sterilization function mainly include $H^+(H_2O)_m$ ions as positive ions and $O_2^-(H_2O)_n$ ions as negative ions.

* * * * *